United States Patent [19]

Sanderson

[11] 4,235,962
[45] Nov. 25, 1980

[54] COMBINATION KIT FOR TRANSAMINASE ASSAY OF A BODY FLUID

[75] Inventor: James S. Sanderson, Indianapolis, Ind.

[73] Assignee: The Dow Chemical Company, Midland, Mich.

[21] Appl. No.: 935,425

[22] Filed: Aug. 21, 1978

[51] Int. Cl.³ .......................... C12Q 1/52; C12Q 1/32
[52] U.S. Cl. ........................................ 435/16; 435/26; 435/810
[58] Field of Search .............. 195/99, 103.5 R; 424/2; 435/16, 26, 805, 810

[56] References Cited

U.S. PATENT DOCUMENTS

| | | | |
|---|---|---|---|
| 3,458,403 | 7/1969 | Katsunuma et al. | 195/103.5 R |
| 3,953,294 | 4/1976 | Monte et al. | 195/103.5 R |
| 4,024,021 | 5/1977 | Stavropoulos et al. | 435/16 |
| 4,086,142 | 4/1978 | Huang et al. | 435/16 |

OTHER PUBLICATIONS

Henry, et al., "Revised Spectrophotometric Methods for the Determination of Glutamic-Oxalacetic Transaminase, Glutamic-Pyruvic Transaminase and Lactic Acid Dehydrogenase", *Am. J. Clin. Path.*, vol. 34, No. 4 (1960), pp. 381–398.
Amador, et al., "Serum Glutamic-Oxaloacetic Transaminase Activity", *Clin. Chem.*, vol. 8, No. 4 (1962), pp. 343–349.
Bergmeyer, et al., "Recommendations of the German Society for Clinical Chem.", *Z. Klin Chem. Biochem.*, vol. 8, No. 6 (1970), pp. 87–88.
Rej, et al., "Effects of Buffers on Aspartate Aminotransferase Activity and Association of the Enzyme with Pyridoxal Phosphate", *Clin. Chem.*, vol. 21, No. 11 (1975), pp. 1585–1591.
Jung, et al., "Effect of Pyridoxyl 5'-Phosphate on the Temperature Relationships of Alanine Aminotransferase", *Clin. Chim. Acta.*, vol. 64, (1975), p. 329.
Bergmeyer, et al., "Empfehlungen der Deutschen Gesellshaft für Klinische Chemre", *Z. Klin. Chem. U. Klin. Biochem.*, vol. 10, (1972), pp. 182–192.
Karmen, et al., "Transaminase Activity in Human Blood", *J. Clin. Invest.*, vol. 34 (1955), pp. 126–131.
Karmen, "A Note on the Spectrophotometric Assay of Glutamic-Oxalacetic Transaminase in Human Blood Serum", *J. Clin. Invest.*, vol. 34 (1955), pp. 131–133.

*Primary Examiner*—Thomas G. Wiseman
*Attorney, Agent, or Firm*—G. D. Street

[57] ABSTRACT

A kit for the determination of transaminase present in body fluid having a first reagent containing aspartate, a second reagent containing alanine, and a third reagent containing 2-oxoglutarate substrate in combination with a secondary reaction system containing reduced nicotinamide adenine dineucleotide.

3 Claims, 2 Drawing Figures

COMBINATION KIT FOR TRANSAMINASE ASSAY OF A BODY FLUID

BACKGROUND OF THE INVENTION

The transaminase enzymes aspartate 2-oxoglutarate aminotransferase, hereafter abbreviated AST, and alanine 2-oxoglutarate aminotransferase, hereafter abbreviated ALT, are found in normal human serum in both the apo (inactive) and holo (active) forms. The holo or active form of the transaminase enzymes contain the coenzyme factor pyridoxal phosphate, hereafter called PLP. The apo or inactive form of the enzymes lack PLP. The holo form of AST catalyzes the transamination between L-aspartate and 2-oxoglutarate to form oxalacetate and glutamate. Similarly, the holo form of ALT catalyzes the transamination between L-alanine and 2-oxoglutarate to form pyruvate and glutamate. Analysis of AST activity in serum is commonly used in the diagnosis of human diseases or disorders such as myocardial infarction, and liver disorders such as toxic hepatitis, cirrhosis, and obstructive jaundice, infectious mononulceosis, acute muscular dystrophy, and acute pancreatitis. Analysis of ALT activity in human serum is used in the diagnosis of liver disease including those mentioned above with the ratio of ALT/AST being employed in further confirmation of liver dysfunction.

An assay for AST was developed by Karmen, J. Clin. Invest. 34, 131 (1955). This method, employing the measurement of oxalacetate using the secondary reaction of malic dehydrogenase and NADH, was modified by Henry, et al., Am. J. Clin. Path, 34, 381 (1960), and Amador and Wacker, Clin. Chem., 8, 343 (1962). Additional modifications including utilization of lactate dehydrogenase to rid the total reaction mixture of endogenous serum pyruvate and the selection of optimum concentrations of aspartate and 2-oxoglutarate for measurement of the isoenzymes of AST were recommended by the German Society of Clinical Chemistry, Z. Klin. Chem. Klin. Biochem. 8, 659 (1970). Most recently, measurement of total AST rather than just the holoenzyme constituency has prompted the utilization by Rej and Vanderline of pyridoxal phosphate in a reaction mixture devoid of phosphate, but including organic buffers such as imidazole, diethenolamine, or tris (hydroxymethyl) methyl aminopropane sulfonic acid (TAPS), Clin. Chem. 21, 1585 (1975).

The key reactions may be summarized as follows:

Inactive apo AST + PLP ⇌ active holo AST  (I)

Aspartate + 2-oxoglutarate $\xrightarrow{\text{Active AST}}$ oxalacetate + glutamate  (II)

Oxalacetate + NADH + H+ $\xrightarrow{\text{Malate dehydrogenase}}$ malate + NAD+  (III)

Pyruvate (endogenous to serum) + NADH + H+ $\xrightarrow{\text{lactate dehydrogenase}}$ lactate + NAD+  (IV)

The measurement of the rate of decrease in NADH concentration as measured at 340 nm is proportional to the AST activity once the endogenous pyruvate has been eliminated by the lactate dehydrogenase reaction.

Likewise, an assay for ALT was developed by Karmen et al., J. Clin. Invest. 34, 126 (1955), employing the measurement of pyruvate using the secondary reaction of lactate dehydrogenase and NADH. Improvements involving selection of optimum concentrations of alanine and 2-oxoglutarate as recommended by the German Society of Clinical Chemistry, Z. Klin. Chem. Klin. Biochem. 10, 182 (1972), and inclusion of PLP for measurement of total ALT, Jung & Egger, Clin. Chim. Acta, 64, 329 (1975) have been made. The key reactions may be summarized as follows:

Inactive apo ALT + PLP ⇌ active holo ALT  (V)

Alanine + 2-oxoglutarate $\xrightarrow{\text{active ALT}}$ pyruvate + glutamate  (VI)

Pyruvate + NADH + H+ $\xrightarrow{\text{lactate dehydrogenase}}$ lactate + NAD+  (VII)

As in the AST activity determination, the measurement of the rate of decrease in NADH concentration as measured in the ultraviolet is proportional to the ALT activity once endogenous serum pyruvate has been eliminated.

SUMMARY OF THE INVENTION

The present invention relates to a kit which may be used to assay for either AST or ALT in a body fluid. The kit also may be used to determine the total amount of transaminase enzyme present, that is both apo and halo forms, or it may be used to assay only for the holo form present in the body fluid. The reagent kit that is the subject of the invention is comprised of three separate reagents—a first aqueous reagent containing aspartate, a second aqueous reagent containing alanine, and a third reagent containing 2-oxoglutarate, reduced nicotinamide adenine dinucleotide (hereafter NADH), malate dehydrogenase (hereafter MDH), and lactate dehydrogenase (hereafter LDH). When the total ALT or AST is assayed, the third reagent will also contain sufficient PLP to reactivate the apo-transaminase. In one embodiment of the present invention the third reagent is lyophilized to achieve a stable reagent composition which will retain satisfactory activity even after reasonable storage.

In order to lyophilize said third reagent composition, it is necessary to add an inert polymer to the reagent to prevent the collapse of the reagent composition during lyophilization. The inert polymer, also referred to as a collapse temperature lowering polymer imparts a unique matrix to the frozen prelyophilized third reagent that allows for efficient removal of adsorbed and nonadsorbed water molecules during the process of lyophilization.

The present invention may be used to assay for either AST or ALT. To use the kit for the assay of AST the first reagent is mixed with the third reagent and a sample of body fluid. The decrease in NADH concentration may be measured on a spectrophotometer or other suitable instrument such as for example an autoanalyzer or fluorometer. The amount of holo AST present in the sample of body fluid is proportional to the rate of NADH decrease in the final reagent/body fluid mixture. See reaction equation IV above.

In a like manner, the kit may be used for the assay of ALT by mixing the second reagent with the third reagent and a sample of body fluid. As indicated by reaction equation VII the rate of decrease in NADH concentration in the final mixture is proportional to the amount of holo-ALT in the original sample of body fluid.

As used in the specification and claims the term "body fluid" refers to any aqueous body fluid which contains transaminase enzyme. The body fluid can be an extract as from a tissue homogenate or the like, or it can be a body fluid such as blood, serum, plasma, lymphatic fluid or the like.

DETAILED DESCRIPTION OF THE INVENTION

Figure 1:
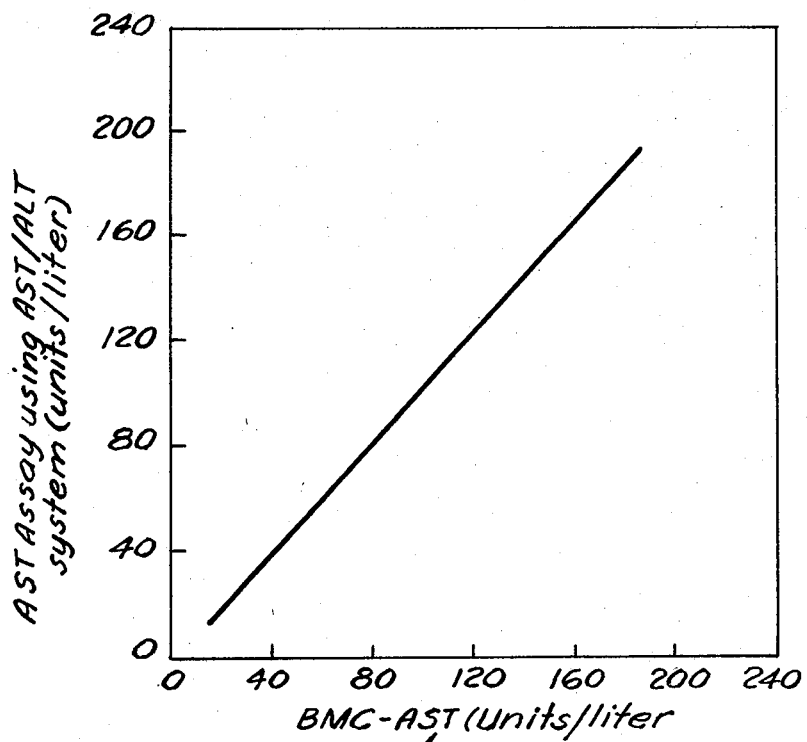
FIG. 1 is a graphic representation comparing the AST values of 52 samples of human serum obtained using the AST/ALT kit that is the subject of this invention with values obtained using a commercially available AST assay kit as a standard.

Prior to the present invention it had not been possible to employ the same 2-oxoglutarate substrate reagent, referred to above as the third reagent, in both the AST and ALT assay. This is because of low levels of both aspartate and alanine which are generally present in normal body fluids. These endogenous amino acid substrates are utilized in the transamination steps of the assay methods (see reaction equations II and IV) to give falsely elevated results.

The present invention, by selecting relatively high concentrations of 2-oxoglutarate in the reagents, exploits the principles of enzyme kinetics to minimize the error due to endogenous amino acid in the sample. Enzyme kinetics indicate that the apparent $K_m$'s (Michaelis constants) of the amino acid substrates of the transaminases increase as the concentration of 2-oxoglutarate increases. Thus the invention by using a high concentration of 2-oxoglutarate minimizes the effect of interference of endogenous alanine and aspartate in the body fluid by necessitating, due to the ping pong mechanism, that the levels of amino acids be much higher to achieve near $V_{max}$ conditions of ALT and AST. This fact coupled with the competitive inhibition of alanine for AST holds cross reactivity to a minimum and prevents falsely elevated values for the assay.

In general, the first reagent must contain sufficient aspartate to yield at least a 35 millimolar concentration in the final reconstitute, i.e. a mixture of the first reagent containing aspartate and the third reagent containing the 2-oxoglutarate substrate. The second reagent must contain sufficient alanine to yield at least a 130 millimolar concentration in the final reconstitute, i.e. a mixture of the second reagent containing aspartate and the third reagent containing the 2-oxoglutarate substrate. The upper limit of concentration for both amino acids is determined by their solubility in the solvent system employed. For practical purposes this is about 1 molar for aspartate and about 1.5 molar for alanine.

In the third reagent or 2-oxoglutarate substrate reagent, sufficient 2-oxoglutarate must be present to yield from about 0.2 to about 35 millimolar concentration in the reconstitute, i.e. a mixture either of reagent one and reagent three or of reagent two and reagent three. In a like manner the concentration of NADH in the reconstitute is from about 0.5 to about 5 millimolar. The concentration of LDH in the final reconstitute is from about 175 units/liter to about 17,500 units/liter and for MDH from about 140 units/liter to about 1,400 units/liter. As used herein one unit of an enzyme refers to the amount of enzyme that will transform one micromole of substrate per minute to its product at 30° C.

In addition, buffers are generally present to maintain the pH at between about 7.5 and 7.8. Suitable buffers include tris(hydroxymethyl)amino methane; imidazole; diethanolamine; tris[(hydroxymethyl)methylaminopropane sulfuric acid]; and the like.

If the third reagent or 2-oxoglutarate substrate is to be lyophilized sufficient inert polymer must be added to allow for the removal of substantially all moisture within a period of about 48 hours without the subsequent collapse of the matrix. One skilled in the art will recognize that the exact concentration of inert polymer in the reagent will depend of factors well known in the art as for example the exact concentration of the various ingredients in the reagent, the collapse temperature of the matrix relative to the various concentrations, the rate of drying, etc. A number of inert polymers have been found to be useful with the present invention such as for example polyvinyl pyrrolidones, polyethylene glycols, and dextrans.

The following examples will serve to further clarify the present invention, but are not to be construed as a limitation thereon.

EXAMPLE 1

The relative concentrations of each of the three reagents making up the kit that is the subject of this invention are given below.

| | |
|---|---|
| A. AST Reconstituting Reagent | |
| L-aspartate | 188 mmol/liter |
| Tris (hydroxymethyl)- amino methane buffer | 50 mmol/liter (pH 7.8) |
| Distilled water | — |
| B. ALT Reconstituting Reagent | |
| L-alanine | 800 mmol/liter |
| Tris(hydroxymethyl)amino- methane buffer | 50 mmol/liter (pH 7.5) |
| Distilled water | — |
| C. 2-Oxoglutarate Substrate | (lyophilized) |
| 2-Oxoglutarate | 15.3 mmol/liter* |
| NADH (yeast) | 0.19 mmol/liter* |
| LDH (animal) | 1800 U/liter* |
| MDH (animal) | 1430 U/liter* |
| Tris[(hydroxymethyl)- methyl amino propane sulfonic acid) | 18 mmol/liter* |
| Polyethylene glycol 8000 | 0.8% by weight |

*concentrations are expressed for wet concentrations of the reconstitute.

EXAMPLE 2

AST determinations may be carried out using the kit of Example 1 by employing the following procedure.
1. (Amount needed) of the 2-oxoglutarate substrate is reconstituted by adding 2.8 ml of the AST reconstituting reagent and swirling the vials gently to completely dissolve the substrate.
2. The reconstitute prepared in Step 1 is preincubated at 30° C. for approximately 10 minutes.
3. 0.20 ml of the serum sample to be assayed is added to the preincubated reconstitute and mixed gently by inversion. Incubation should be continued.
4. One minute after the addition of the serum sample, the absorbance is read on a spectrophotometer or equivalent instrument at an absorbance value of between about 334 and 360 nanometers and at one minute intervals thereafter for three minutes.
5. The decrease in absorbance per minute ($\Delta A$/min) is calculated from the results of Step 4 above.

EXAMPLE 3

ALT determinations may be carried out using the kit of Example 1 using the following procedure.
1. (Amount needed) of the 2-oxoglutarate substrate is reconstituted by adding 2.8 ml of the ALT reconstituting reagent and swirling the vials gently to completely dissolve the substrate.

Remaining Steps 2 through 5 are identical to Steps 2 through 5 in Example 2 above.

In determining the total (apo and holo) transaminase present in the serum using the procedures of Examples 2 and 3 sufficient PLP must be added prior to recording of activity to reactivate the apo-transaminase present. Generally from about 0.01 to about 0.30 mmole of PLP per liter of reaction system is sufficient. The PLP is most conveniently added to $\alpha$-oxoglutate substrate lyophilizate.

In calculating the amount of transaminase in the sample of body fluid the following formula is used $$\text{Amount of Transaminase in Units/liter} = \frac{\Delta A/\text{min.} \times 1000 \times T_f \times V_x \times 100}{\epsilon \times V_s \times b}$$

wherein
- $\epsilon$ = molar absorptivity for NADH (at 340 nm $\epsilon = 6.22 \times 10^3$)
- $*T_f$ = Temperature correction factor
- $*V_x$ = Volume of the reaction mixture in ml.
- $b$ = Light path length in cm of the reaction vial or cuvette
- $*V_s$ = ml of specimen used

*note when $T_f$ is 1.0, $V_x$ is 3.0 ml and $V_s$ is 0.20 ml.

EXAMPLE 4

Using the kit shown in Example 1 with the general procedure described in Example 2, 52 samples of human serum were assayed for AST. The results obtained using the kit described herein were compared to a commercially available AST assay system sold by Boehringer Mannheim Corporation which served as a standard. The correlation between the results obtained using the two methods is shown in FIG. 1. Regression analysis of the data using the two systems gave slope 1.038, intercept $-0.798$, and correlation coefficient 0.996.

EXAMPLE 5

Figure 2:
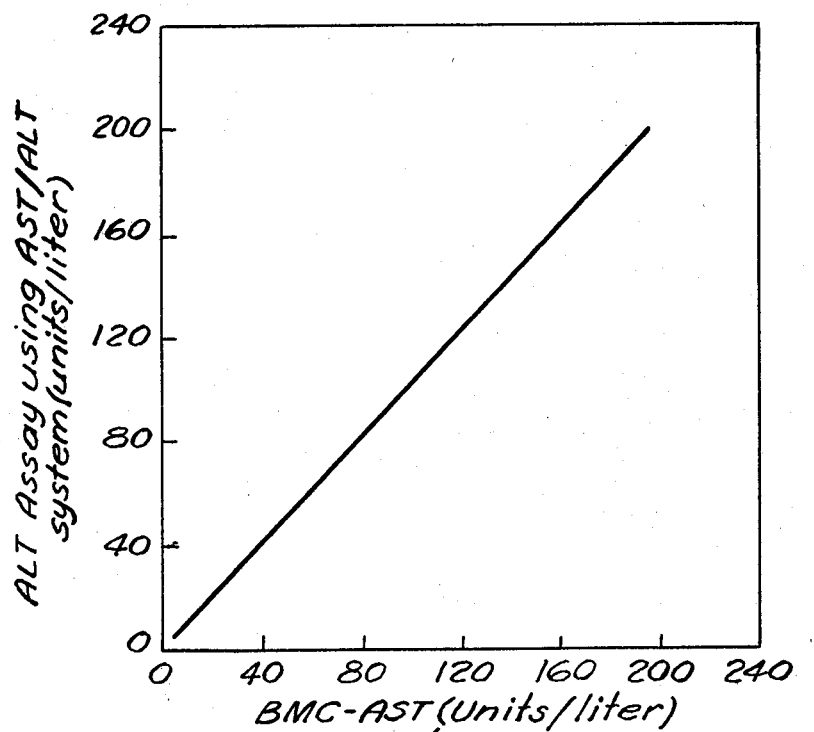
FIG. 2 is a graphic representation comparing the ALT values of 56 samples of human serum obtained using the AST/ALT kit that is the subject of this invention with values obtained using a commercially available ALT assay kit as standard.

Using the kit shown in Example 1 with the general procedure described in Example 3, 56 samples of human serum were assayed for ALT. The results obtained using the kit described herein was compared to a commercially available ALT assay systems sold by Boehringer Mannheim Corporation which served as a standard. The correlation between the results obtained using the two methods is shown in FIG. 2. Regression analysis of the data using the two systems gave slope 1.061, intercept 0.178 and correlation coefficient 0.998.

The data obtained from Examples 4 and 5 as shown graphically in FIGS. 1 and 2 clearly demonstrate the close correlation between the results of assay for AST and ALT using the AST/ALT kit that is the subject of this invention and separate commercially recognized standard systems for the assay of AST and ALT.

In elucidating the principles underlying the present invention an examination of the enzyme kinetics used to minimize the effect of the endogenous amino acids on the transaminases being measured is necessary.

Using standard nomenclature and representational presentations, a typical ping pong bi enzyme mechanism is expressed schematically as follows:

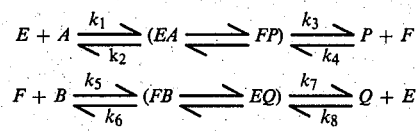

where:
(a) A and B are substrates in order of addition, A being aspartate in the case of AST.
(b) P and Q are products in order of release, P being glutamate in the case of AST.
(c) E and F are enzyme forms incapable of unimolecular reaction resulting in liberation of substrate or product.
(d) EA, FP, FB, and EQ are transitory complexes capable of unimolecular reaction resulting in liberation of substrate or product.
(e) $k_i$ = rate constants for any given directional reaction as indicated by the arrows over which they appear.

The complete rate equation describing such a mechanism of catalysts can be expressed as follows:

$$v = \frac{V_1 V_2 (AB - \frac{PQ}{K_{eq}})}{K_B V_2 A + K_A V_2 B + V_2 AB + \frac{K_q V_1 P}{K_{eq}} + \frac{K_p V_1 Q}{K_{eq}} + \frac{V_1}{K_{eq}} PQ + \frac{K Q V_1}{K_{iA} K_{eq}} AP + \frac{K_A V_2 BQ}{K_{iQ}}}$$

For measurement of initial velocities $v_i$ as is the case in the enzyme activity determinations of the transaminases under discussion, the rate equation is simplified owing to all terms involving P and Q being negligible. Such an equation is expressed as follows:

$$v_i = \frac{V_1 AB}{K_A B + K_B A + AB}$$

Consider the situation at any given concentration of B (i.e. oxoglutarate in the case of AST) By definition, when $$1/v_i = 0, 1/A = [-\frac{1}{V_1} - \frac{K_B}{V_1 B}]\frac{V_1}{K_A} = -\frac{1}{\text{apparent Km of } A}$$

therefore the apparent $$K_{mA} = \frac{K_A}{1 = K_B/B}$$

From this expression it can be seen that, for a ping pong mechanism, the apparent $K_m$ of A increases as the concentration of B increases.

In reducing the last expression to practical simplistic terms, one need only consider the situation described in measurement of rates of physiological important enzymes (i.e. at near Vmax (i.e. $V_1$) conditions where the enzyme rate of measurement is proportional to the enzyme concentration owing to the substrate concentration being so sufficient as to be kinetically non-limiting in the course of measurement of enzyme levels across the whole breadth of activities found in normal and physiological disease states.

For precise measurement of a bimolecular reaction of the type under discussion, the rate of a reaction, at a given "B" concentration should be independent of A's concentration (i.e. at or near apparent Vmax with respect to A). However, for situations where A's concentrations are very low (i.e. endogenous serum contributions of amino acids in a side reaction situation) it becomes important to be able to access the extent of measurement of the apparent maximum velocity of said "contaminant reaction." This being the case of a combination AST/ALT test where one is concerned with the measurement of AST in an ALT test or vice versa, a mathematical outline is in order. Both side reactions are quantitatively discussed below.

A. AST cross measurement in an ALT test for a ping pong mechanism, $$V_i = \frac{V_1}{\frac{K_A}{A} + \frac{K_B}{B} + 1}$$

Assume B (i.e. αketoglutarate, 2-oxoglutarate) $>>K_B$

Note: $K_B=0.1$ mM [S. F. Velick & J. Vavra, *The Enzymes*, 6, 219 (1962)]

$$V_i = \frac{V_1 \text{ Apparent } (A)}{K_A \text{ Apparent } + (A)}$$

Observations of competitive inhibition, by alanine for the same form of the AST enzyme E that binds aspartate, produces the following additional mathematical constraint:

$$V_i = \frac{V_1 \text{ Apparent } (A)}{K_A \text{ Apparent } (1 + \frac{I}{K_i}) + (A)}$$

where:
I = competitive inhibitor alanine concentration
$K_i$ = inhibition constant For the contaminant reaction of AST in an ALT measurement, at 0.0016 mM aspartate, the normal endogenous serum aspartate concentration in the reaction system, at an experimentally determined apparent $Km_A$ of 10 mM at 15 mM 2-oxoglutarate, at a level of 800 mM alanine present when one measures ALT function of the combination test, and with an experimentally determined $K_i$ of alanine of 400 mM determined under the 15 mM 2-oxoglutarate conditions, the above expression becomes:

$$V_i = \frac{V_1 \text{ Apparent } (0.0016 \text{ mM})}{10 \text{ mM } (1 + \frac{800 \text{ mM}}{400 \text{ mM}}) + 0.0016 \text{ mM}}$$

% $V_1$ Apparent as measured $V_1 = 0.0054\%$

For descriptive purposes, the apparent Km of aspartate of AST likewise measured at a lower 2-oxoglutarate level, 0.2 mM, was found to be 0.91 mM. Going through the same mathematical explanation:

$$V_i = \frac{V_1}{\frac{K_A}{A} + \frac{K_B}{B} + 1}$$

Here B (i.e. 2-oxoglutarate) is not $>>K_B$ but at a given (A) of 0.0016 mM, $(K_B/B)+1$ is $<<K_A/A$ since:
$K_A=0.90$ mM and $K_B=0.1$ mM [S. Valeck and J. Vavra, *The Enzymes*, 6, 219 (1962)]

$$V_i = \frac{V_1 \text{ Apparent}}{\frac{K_A \text{ Apparent}}{A}} + (1 + I/K_i)$$

$$V_i = \frac{V_1 \text{ Apparent}}{\frac{0.90 \text{ mM}}{0.0016 \text{ mM}} + (1 + \frac{800 \text{ mM}}{400 \text{ mM}})}$$

$$V_i = \frac{V_1 \text{ Apparent}}{1700}$$

$V_i = 0.059\% \; V_1$ Apparent

Consequently, in this example shown above, the % of maximum apparent turnover, under two different levels of 2-oxoglutarate, at endogenous contributing serum levels of aspartate expected to be found upon measurement of ALT rather than AST in combination ALT/AST system, varies by ≈10 fold.

B. ALT cross measurement in an AST test

ALT, likewise having a "ping pong" mechanism of catalysis, can kinetically be described identically:

$$V_i = \frac{V_1}{\frac{K_A}{A} + \frac{K_B}{B} + 1}$$

Disregarding the possible inhibition of ALT by aspartate as noted in Table I, at 0.060 mM alanine, the normal level contributed by serum corrected for the dilution in the reaction mixture using an apparent $K_m$ of alanine of 18.1 mM measured at 15 mM 2-oxoglutarate where $K_B$ (i.e. oxoglutarate)=0.4 mM [Saier, M. H., Jr., and Jenkins, W. T., J. Biol. Chem., 242, 91 (1967)] $(K_B/B+1$ is again $<<K_A/A$.

Therefore the $$V_i = \frac{V_1 \text{ Apparent}}{\frac{K_A \text{ Apparent}}{A}}$$

$$V_i = \frac{V_1 \text{ Apparent}}{300}$$

% $V_1$ apparent is measured $V_i = 0.33\%$

Likewise, at a lower 2-oxoglutarate concentration of 0.02 mM where $K_m$ apparent of alanine=45 mM, $$\frac{K_A}{A} << \frac{K_B}{B} + 1.$$

Therefore the % $V_1$ apparent as measured $$V_i = \frac{V_1 \text{ Apparent}}{45/0.06} \times 100\% = 1.3\%.$$

TABLE 1

SUMMARY OF KINETIC STUDIES ON THE SPECIFICITY OF THE AST/ALT SYSTEM

| SYSTEM | KINETIC PARAMETERS | VALUE |
|---|---|---|
| AST | Apparent $K_m$ of aspartate @ 15 mM 2-oxoglutarate | 10 mM |
|  | Apparent $K_i$ of alanine for AST @15 mM 2-oxoglutarate | 400 mM |
|  | *Contribution of aspartate endogenous to serum | 0.0016 mM |
|  | Theoretical turnover of AST at above level of serum contributing aspartate, 15 mM 2-oxoglutarate, and 800 mM alanine (% $V_{mdx}$) | 0.016% |
| ALT | Apparent $K_m$ of alanine for ALT at 15 mM 2-oxoglutarate | 18.1 mM |
|  | Apparent $K_i$ of aspartate for ALT at 15 mM 2-oxoglutarate | >2000 mM[4] |
| (ALT) | **Contribution of alanine endogenous to serum | 0.060 mM |
|  | Theoretical turnover of ALT at above level of serum contributing alanine, 15 mM 2-oxoglutarate, and 186 mM aspartate (% $V_{max}$) | 0.33% |

[1]NOTE:
For apparent $K_m$ of alanine of 4.5 mM at 0.2 mM 2-oxoglutarate, theoretical turnover of ALT at 0.060 mM alanine is 1.32% $V_{max}$.
[2]Principles of Biochemistry, White, A, Handler, P., and Smith, E., eds., McGraw-Hill, New York, (1968), p. 706.
[3]Owing to ping-pong mechanism of catalysis, the greater the [oxoglutarate] the greater the $K_m$ for the amino acid substrate and hence, the less interference from cross reactivity due to sample endogenous amino acids.
[4]$K_i$ is so large as to have a negligible effect in the calculations and may be due to artifactual ionic strength effects.
[5]NOTE:
For apparent measured $K_m$ of aspartate of 0.91 mM at 0.2 mM 2-oxoglutarate, theoretical turnover of AST at 0.0016 mM asparate is 0.1% $V_{max}$.

What is claimed is:

1. A reagent kit for the determination of transaminase present in a body fluid comprising a first reagent containing aspartate, a second reagent containing alanine, and a third reagent containing 2-oxoglutarate, reduced nicotinamide adenine dinucleotide (NADH), malate dehydrogenase (MDH), and lactate dehydrogenase (LDH) wherein the amounts of each reagent used are sufficient to provide, upon direct mixing of said first reagent with said third reagent, a resulting mixture containing at least 35 millimolar concentration of aspartate, from about 0.2 to about 35 millimolar concentration of 2-oxoglutarate, from about 0.5 to about 5 millimolar concentration of reduced NADH, at least 175 units/liter of LDH and at least 140 units/liter of MDH and upon direct mixing of, said second reagent with said third reagent, to provide a resulting mixture containing at least 130 millimolar alanine, from about 0.2 to about 35 millimolar concentration of 2-oxoglutarate, from about 0.5 to about 5 millimolar concentration of reduced NADH, at least 175 units/liter of LDH and at least 140 units/liter of MDH.

2. The kit of claim 1 wherein sufficient pyridoxal phosphate is present in said third reagent to reactivate substantially all apo-transaminase in a sample of body fluid tested for total transaminase activity.

3. The kit of claim 1 wherein said third reagent is lyophilized.

* * * * *

UNITED STATES PATENT AND TRADEMARK OFFICE
CERTIFICATE OF CORRECTION

PATENT NO. : 4,235,962
DATED : November 25, 1980
INVENTOR(S) : James S. Sanderson It is certified that error appears in the above-identified patent and that said Letters Patent are hereby corrected as shown below:

First page, beside [75] Inventor's name should read, --James A. Sanderson--.

Column 1, line 23, "cirrhosis, and" should read --cirrhosis,

Column 2, line 27, "halo" should read --holo--.

Column 6, line 48, "catalysts" should read --catalysis--.

Column 6, between lines 49 and 57, after equation, footnotes as follows were left out:

-- Where: $v$ = velocity of the reaction at any point in time after attaining steady-state $V_1$ = maximum velocity in the forward direction $V_2$ = maximum velocity in the reverse direction $K_A, K_B$ --- = Michaelis constants for A,B,---

$K_{iA}$ and $K_{iq}$ = Inhibition constants for A and Q respectively $K_{eq}$ = thermodynamic equilibrium constant. --

UNITED STATES PATENT AND TRADEMARK OFFICE
CERTIFICATE OF CORRECTION

PATENT NO. : 4,235,962
DATED : November 25, 1980
INVENTOR(S) : James S. Sanderson It is certified that error appears in the above-identified patent and that said Letters Patent are hereby corrected as shown below:

Column 8, line 14, in equation, line should read -- % $V_1$ Apparent as measured $V_i$ = 0.0054% --.

Column 9, Table 1, last line under Subtitle KINETIC PARAMETERS but before line Subtitle SYSTEM ALT, should read --aspartate, 15 mM 2-oxoglutarate, and 800 mM alanine (% $V_{max}$)--.

Signed and Sealed this

Fifteenth Day of September 1981

[SEAL]

Attest:

Attesting Officer

GERALD J. MOSSINGHOFF

Commissioner of Patents and Trademarks